(12) United States Patent
Mander et al.

(10) Patent No.: US 9,664,610 B2
(45) Date of Patent: May 30, 2017

(54) SYSTEMS FOR FLUID ANALYSIS USING ELECTROMAGNETIC ENERGY THAT IS REFLECTED A NUMBER OF TIMES THROUGH A FLUID CONTAINED WITHIN A REFLECTIVE CHAMBER

(71) Applicant: Visualant, Inc., Seattle, WA (US)

(72) Inventors: Richard Ian Mander, Bainbridge Island, WA (US); Thomas A. Furness, III, Seattle, WA (US); Michael Vivian Denton, Christchurch (NZ); Allan David Beach, Prebbleton (NZ)

(73) Assignee: Visualant, Inc., Seattle, WA (US)

( * ) Notice: Subject to any disclaimer, the term of this patent is extended or adjusted under 35 U.S.C. 154(b) by 0 days.

(21) Appl. No.: 14/206,055

(22) Filed: Mar. 12, 2014

(65) Prior Publication Data
US 2014/0333920 A1 Nov. 13, 2014

Related U.S. Application Data

(60) Provisional application No. 61/777,750, filed on Mar. 12, 2013.

(51) Int. Cl.
*G01N 21/01* (2006.01)
*G01N 21/3504* (2014.01)
(Continued)

(52) U.S. Cl.
CPC .......... *G01N 21/01* (2013.01); *G01N 21/031* (2013.01); *G01N 21/274* (2013.01);
(Continued)

(58) Field of Classification Search
CPC .... G01N 21/65; G01N 21/01; G01N 21/3504; G01N 21/031; G01N 21/274;
(Continued)

(56) References Cited

U.S. PATENT DOCUMENTS

| 3,499,158 A | 3/1970 | Lavine et al. |
| 3,504,164 A | 3/1970 | Farrell et al. |

(Continued)

FOREIGN PATENT DOCUMENTS

| EP | 2 266 630 A1 | 12/2010 |
| GB | 1 470 737 | 4/1977 |

(Continued)

OTHER PUBLICATIONS

"Color Technology Beyond the Visible Spectrum Creating Solutions for Product Authentication: Extraordinary Investment Opportunity & 12 month Roadmap," Visualant Inc., Seattle, Washington, Nov. 17, 2006, 10 pages.

(Continued)

*Primary Examiner* — Michael P Lapage
(74) *Attorney, Agent, or Firm* — Seed IP Law Group LLP (57) ABSTRACT

Systems for analyzing fluids (e.g., gases) include a chamber structure with a reflective inner surface, emitters, a primary detector positioned to principally detect electromagnetic energy reflected numerous times through the gas(es) and a calibration detector positioned to detect electromagnetic energy not reflected numerous times through the gas(es). Calibration may be automatically performed. The primary detector relies principally on Raleigh scattering. An optional primary detector may be positioned to principally detect Raman scattered electromagnetic energy.

18 Claims, 5 Drawing Sheets

(51) Int. Cl.
   *G01N 21/03* (2006.01)
   *G01N 21/27* (2006.01)
   *G01N 21/51* (2006.01)
   *G01N 21/65* (2006.01)
   *G01J 3/44* (2006.01)

(52) U.S. Cl.
   CPC ......... *G01N 21/3504* (2013.01); *G01N 21/51* (2013.01); *G01N 21/65* (2013.01); *G01J 3/44* (2013.01); *G01N 2021/0106* (2013.01); *G01N 2021/513* (2013.01); *G01N 2021/516* (2013.01)

(58) Field of Classification Search
   CPC ............. G01N 21/51; G01N 2021/516; G01N 2021/513; G01N 2021/0106; G01J 3/44
   See application file for complete search history.

(56) References Cited

U.S. PATENT DOCUMENTS

| | | | |
|---|---|---|---|
| 3,556,659 | A * | 1/1971 | Hewes .................. G01N 21/65 356/246 |
| 3,582,659 | A | 6/1971 | Dekker |
| 3,679,449 | A | 7/1972 | Nagot et al. |
| 3,822,098 | A | 7/1974 | Rudder et al. |
| 3,867,039 | A | 2/1975 | Nelson |
| 3,922,090 | A | 11/1975 | Fain |
| 3,942,185 | A | 3/1976 | Lebailly |
| 3,994,590 | A | 11/1976 | Di Martini et al. |
| 3,994,603 | A * | 11/1976 | Paschedag ........... G08B 17/103 250/575 |
| 4,082,188 | A | 4/1978 | Grimmell et al. |
| 4,098,940 | A | 7/1978 | Groh et al. |
| 4,120,445 | A | 10/1978 | Carrier et al. |
| 4,183,989 | A | 1/1980 | Tooth |
| 4,241,738 | A | 12/1980 | Lübbers et al. |
| 4,277,514 | A | 7/1981 | Sugiura et al. |
| 4,325,981 | A | 4/1982 | Sugiura et al. |
| 4,531,117 | A | 7/1985 | Nourse et al. |
| 4,547,869 | A | 10/1985 | Savit |
| 4,652,913 | A | 3/1987 | Saitoh et al. |
| 4,678,338 | A | 7/1987 | Kitta et al. |
| 4,760,250 | A | 7/1988 | Loeppert |
| 4,830,501 | A | 5/1989 | Terashita |
| 4,921,278 | A | 5/1990 | Shiang et al. |
| 4,952,061 | A | 8/1990 | Edgar |
| 5,024,526 | A * | 6/1991 | von Redwitz ......... G01N 21/53 356/339 |
| 5,137,364 | A | 8/1992 | McCarthy |
| 5,304,813 | A | 4/1994 | De Man |
| 5,325,167 | A | 6/1994 | Melen |
| 5,353,052 | A | 10/1994 | Suzuki et al. |
| 5,377,000 | A | 12/1994 | Berends |
| 5,576,627 | A | 11/1996 | McEwan |
| 5,619,326 | A | 4/1997 | Takamatsu et al. |
| 5,637,275 | A | 6/1997 | Carey et al. |
| 5,816,874 | A | 10/1998 | Juran et al. |
| 5,821,405 | A | 10/1998 | Dickey et al. |
| 5,844,680 | A | 12/1998 | Sperling |
| 5,924,981 | A | 7/1999 | Rothfritz et al. |
| 5,926,282 | A | 7/1999 | Knobloch et al. |
| 5,933,244 | A | 8/1999 | Kiritchenko |
| 5,946,066 | A | 8/1999 | Lee et al. |
| 5,966,217 | A | 10/1999 | Roe et al. |
| 5,969,814 | A | 10/1999 | Barber et al. |
| 6,020,583 | A | 2/2000 | Walowit et al. |
| 6,035,246 | A | 3/2000 | Wagner |
| 6,038,024 | A | 3/2000 | Berner |
| 6,054,021 | A | 4/2000 | Kurrle et al. |
| 6,121,627 | A | 9/2000 | Tulip |
| 6,122,042 | A | 9/2000 | Wunderman et al. |
| 6,142,629 | A | 11/2000 | Adel et al. |
| 6,165,609 | A | 12/2000 | Curatolo |
| 6,172,745 | B1 | 1/2001 | Voser et al. |
| 6,176,522 | B1 | 1/2001 | Jackson |
| 6,255,948 | B1 | 7/2001 | Wolpert et al. |
| 6,384,918 | B1 | 5/2002 | Hubble, III et al. |
| 6,421,553 | B1 | 7/2002 | Costa et al. |
| 6,437,326 | B1 | 8/2002 | Yamate et al. |
| 6,439,688 | B1 | 8/2002 | Vives et al. |
| 6,449,045 | B1 | 9/2002 | Mestha |
| 6,494,557 | B1 | 12/2002 | Kato et al. |
| 6,556,932 | B1 | 4/2003 | Mestha et al. |
| 6,560,352 | B2 | 5/2003 | Rowe et al. |
| 6,560,546 | B1 | 5/2003 | Shenk et al. |
| 6,584,435 | B2 | 6/2003 | Mestha et al. |
| 6,621,576 | B2 | 9/2003 | Tandon et al. |
| 6,633,382 | B2 | 10/2003 | Hubble, III et al. |
| 6,639,699 | B2 | 10/2003 | Matsuyama |
| 6,690,465 | B2 | 2/2004 | Shimizu et al. |
| 6,718,046 | B2 | 4/2004 | Reed et al. |
| 6,721,440 | B2 | 4/2004 | Reed et al. |
| 6,721,629 | B2 | 4/2004 | Wendling et al. |
| 6,724,912 | B1 | 4/2004 | Carr et al. |
| 6,731,785 | B1 | 5/2004 | Mennie et al. |
| 6,744,909 | B1 | 6/2004 | Kostrzewski et al. |
| 6,748,533 | B1 | 6/2004 | Wu et al. |
| 6,757,406 | B2 | 6/2004 | Rhoads |
| 6,763,124 | B2 | 7/2004 | Alattar et al. |
| 6,765,663 | B2 | 7/2004 | Byren et al. |
| 6,782,115 | B2 | 8/2004 | Decker et al. |
| 6,788,800 | B1 | 9/2004 | Carr et al. |
| 6,798,517 | B2 | 9/2004 | Wagner et al. |
| 6,804,376 | B2 | 10/2004 | Rhoads et al. |
| 6,804,377 | B2 | 10/2004 | Reed et al. |
| 6,809,855 | B2 | 10/2004 | Hubble, III et al. |
| 6,819,775 | B2 | 11/2004 | Amidror et al. |
| 6,832,003 | B2 | 12/2004 | McGrew |
| 6,835,574 | B2 | 12/2004 | Neilson et al. |
| 6,870,620 | B2 | 3/2005 | Faupel et al. |
| 6,882,737 | B2 | 4/2005 | Lofgren et al. |
| 6,888,633 | B2 | 5/2005 | Vander Jagt et al. |
| 6,930,773 | B2 | 8/2005 | Cronin et al. |
| 6,937,323 | B2 | 8/2005 | Worthington et al. |
| 6,968,337 | B2 | 11/2005 | Wold |
| 6,980,704 | B2 | 12/2005 | Kia et al. |
| 6,992,775 | B2 | 1/2006 | Soliz et al. |
| 6,993,535 | B2 | 1/2006 | Bolle et al. |
| 6,995,839 | B1 | 2/2006 | Shapiro |
| 6,996,478 | B2 | 2/2006 | Sunshine et al. |
| 7,001,038 | B2 | 2/2006 | Bock et al. |
| 7,003,132 | B2 | 2/2006 | Rhoads |
| 7,003,141 | B1 | 2/2006 | Lichtermann et al. |
| 7,005,661 | B2 | 2/2006 | Yamaguchi et al. |
| 7,006,204 | B2 | 2/2006 | Coombs et al. |
| 7,008,795 | B2 | 3/2006 | Yerazunis et al. |
| 7,012,695 | B2 | 3/2006 | Maier et al. |
| 7,016,717 | B2 | 3/2006 | Demos et al. |
| 7,018,204 | B2 | 3/2006 | Jung et al. |
| 7,023,545 | B2 | 4/2006 | Slater |
| 7,026,600 | B2 | 4/2006 | Jamieson et al. |
| 7,027,134 | B1 | 4/2006 | Garcia-Rubio et al. |
| 7,027,165 | B2 | 4/2006 | De Haas et al. |
| 7,027,619 | B2 | 4/2006 | Pavlidis et al. |
| 7,031,555 | B2 | 4/2006 | Troyanker |
| 7,032,988 | B2 | 4/2006 | Darby et al. |
| 7,035,873 | B2 | 4/2006 | Weare |
| 7,038,766 | B2 | 5/2006 | Kerns et al. |
| 7,041,362 | B2 | 5/2006 | Barbera-Guillem |
| 7,044,386 | B2 | 5/2006 | Berson |
| 7,046,346 | B2 | 5/2006 | Premjeyanth et al. |
| 7,046,842 | B2 | 5/2006 | Lin et al. |
| 7,049,597 | B2 | 5/2006 | Bodkin |
| 7,052,730 | B2 | 5/2006 | Patel et al. |
| 7,052,920 | B2 | 5/2006 | Ushio et al. |
| 7,058,200 | B2 | 6/2006 | Donescu et al. |
| 7,058,530 | B1 | 6/2006 | Miller et al. |
| 7,061,652 | B2 | 6/2006 | Kurita et al. |
| 7,063,260 | B2 | 6/2006 | Mossberg et al. |
| 7,130,444 | B2 | 10/2006 | Housinger et al. |
| 7,154,603 | B2 | 12/2006 | Banks |
| 7,155,068 | B2 | 12/2006 | Zhang et al. |
| 7,170,606 | B2 | 1/2007 | Yerazunis |

(56) References Cited

U.S. PATENT DOCUMENTS

| | | |
|---|---|---|
| 7,171,680 B2 | 1/2007 | Lange |
| 7,252,241 B2 | 8/2007 | Yamada |
| 7,259,853 B2 | 8/2007 | Hubble, III et al. |
| 7,285,158 B2 | 10/2007 | Iwanami et al. |
| 7,307,752 B1 | 12/2007 | Mestha et al. |
| 7,313,427 B2 | 12/2007 | Benni |
| 7,317,814 B2 | 1/2008 | Kostrzewski et al. |
| 7,319,775 B2 | 1/2008 | Sharma et al. |
| 7,359,804 B2 | 4/2008 | Williams et al. |
| 7,383,261 B2 | 6/2008 | Mestha et al. |
| 7,406,184 B2 | 7/2008 | Wolff et al. |
| 7,440,620 B1 | 10/2008 | Aartsen |
| 7,474,407 B2 | 1/2009 | Gutin |
| 7,483,548 B2 | 1/2009 | Nakano et al. |
| 7,570,988 B2 | 8/2009 | Ramanujam et al. |
| 7,616,317 B2 | 11/2009 | Misener et al. |
| 7,733,490 B2 | 6/2010 | Goodwin et al. |
| 7,738,235 B2 | 6/2010 | Gloisten et al. |
| 7,830,510 B2 | 11/2010 | Liu et al. |
| 7,996,173 B2 | 8/2011 | Schowengerdt et al. |
| 8,003,945 B1* | 8/2011 | Wong .................. G01J 5/0014 250/343 |
| 8,064,286 B2 | 11/2011 | Rønnekleiv et al. |
| 8,076,630 B2 | 12/2011 | Schowengerdt et al. |
| 8,081,304 B2 | 12/2011 | Furness, III et al. |
| 8,118,983 B1 | 2/2012 | Anderson et al. |
| 8,178,832 B1* | 5/2012 | Wong .................. G01N 21/274 250/252.1 |
| 8,285,510 B2 | 10/2012 | Schowengerdt et al. |
| 8,368,878 B2 | 2/2013 | Furness, III et al. |
| 8,542,418 B2 | 9/2013 | Chandu et al. |
| 8,583,394 B2 | 11/2013 | Schowengerdt et al. |
| 8,718,939 B2 | 5/2014 | Hamann et al. |
| 8,796,627 B2 | 8/2014 | Rockwell et al. |
| 8,872,133 B2 | 10/2014 | Schreiber et al. |
| 2001/0041843 A1 | 11/2001 | Modell et al. |
| 2002/0146146 A1 | 10/2002 | Miolla et al. |
| 2003/0026762 A1 | 2/2003 | Malmros et al. |
| 2003/0031347 A1 | 2/2003 | Wang |
| 2003/0037602 A1 | 2/2003 | Glasgow, Jr. et al. |
| 2003/0045798 A1 | 3/2003 | Hular et al. |
| 2003/0063772 A1 | 4/2003 | Smith et al. |
| 2003/0092393 A1 | 5/2003 | Tokhtuev et al. |
| 2003/0151611 A1 | 8/2003 | Turpin et al. |
| 2003/0156752 A1 | 8/2003 | Turpin et al. |
| 2003/0158617 A1 | 8/2003 | Turpin et al. |
| 2003/0158788 A1 | 8/2003 | Turpin et al. |
| 2003/0174882 A1 | 9/2003 | Turpin et al. |
| 2003/0235919 A1* | 12/2003 | Chandler .......... G01N 15/1456 422/82.05 |
| 2004/0064053 A1 | 4/2004 | Chang et al. |
| 2004/0071311 A1 | 4/2004 | Choi et al. |
| 2004/0101158 A1 | 5/2004 | Butler |
| 2004/0101159 A1 | 5/2004 | Butler |
| 2004/0142484 A1 | 7/2004 | Berlin et al. |
| 2005/0094127 A1 | 5/2005 | O'mahony et al. |
| 2005/0213092 A1 | 9/2005 | MacKinnon et al. |
| 2006/0013454 A1 | 1/2006 | Flewelling et al. |
| 2006/0047445 A1 | 3/2006 | Williams et al. |
| 2006/0059013 A1 | 3/2006 | Lowe |
| 2006/0077392 A1 | 4/2006 | Hebert et al. |
| 2006/0161788 A1 | 7/2006 | Turpin et al. |
| 2007/0078610 A1 | 4/2007 | Adams et al. |
| 2007/0114421 A1* | 5/2007 | Maehlich .......... G01N 21/0303 250/343 |
| 2007/0222973 A1 | 9/2007 | Hoshiko et al. |
| 2007/0265532 A1 | 11/2007 | Maynard et al. |
| 2008/0061238 A1* | 3/2008 | Hok .................. G01N 21/3504 250/340 |
| 2008/0171925 A1 | 7/2008 | Xu et al. |
| 2008/0212087 A1 | 9/2008 | Mannhardt et al. |
| 2008/0233008 A1* | 9/2008 | Sarkisov ............. G01N 21/77 422/82.05 |
| 2008/0252066 A1 | 10/2008 | Rapoport et al. |
| 2009/0046285 A1* | 2/2009 | Kang .................. G01N 21/031 356/311 |
| 2009/0075391 A1 | 3/2009 | Fulghum, Jr. |
| 2009/0268204 A1* | 10/2009 | Tkachuk .......... G01N 21/3504 356/437 |
| 2010/0085569 A1 | 4/2010 | Liu et al. |
| 2010/0302546 A1* | 12/2010 | Azimi .................. G01J 3/02 356/437 |
| 2011/0192592 A1 | 8/2011 | Roddy et al. |
| 2011/0223655 A1 | 9/2011 | Lapota et al. |
| 2011/0235041 A1 | 9/2011 | Rao et al. |
| 2012/0037817 A1 | 2/2012 | Vondras et al. |
| 2012/0072176 A1 | 3/2012 | Schowengerdt et al. |
| 2012/0223130 A1 | 9/2012 | Knopp et al. |
| 2012/0288951 A1 | 11/2012 | Acharya et al. |
| 2013/0208260 A1 | 8/2013 | Furness, III et al. |
| 2013/0215168 A1 | 8/2013 | Furness, III et al. |
| 2013/0221224 A1* | 8/2013 | Maksyutenko .... G01N 21/0303 250/343 |
| 2013/0334044 A1 | 12/2013 | Brown |
| 2014/0063239 A1 | 3/2014 | Furness, III et al. |
| 2014/0183362 A1 | 7/2014 | Islam |
| 2014/0203184 A1 | 7/2014 | Purdy et al. |
| 2015/0096369 A1 | 4/2015 | Sickels, Jr. |

FOREIGN PATENT DOCUMENTS

| | | |
|---|---|---|
| JP | 10-508940 A | 9/1998 |
| JP | 2005-214835 A | 8/2005 |
| WO | 91/05459 A1 | 5/1991 |
| WO | 96/07886 A1 | 3/1996 |
| WO | 00/12229 A1 | 3/2000 |
| WO | 03/069884 A2 | 8/2003 |
| WO | 2004/089640 A2 | 10/2004 |
| WO | 2006/050367 A2 | 5/2006 |
| WO | 2008/016590 A2 | 2/2008 |
| WO | 2013/043737 A1 | 3/2013 |
| WO | 2013/119822 A1 | 8/2013 |
| WO | 2013/119824 A1 | 8/2013 |
| WO | 2014/121267 A2 | 8/2014 |
| WO | 2014/130857 A1 | 8/2014 |

OTHER PUBLICATIONS

Cri Nuance Multispectral Imaging System, URL=http://www.cri-inc.com/products/nuance.asp, download date Jan. 30, 2007, 2 pages.

Cri Products Components, URL=http://www.cri-inc.com/products/components.asp, download date Jan. 30, 2007, 5 pages.

Furness III, "Systems, Methods and Articles Related to Machine-Readable Indicia and Symbols," U.S. Appl. No. 61/597,593, filed Feb. 10, 2012, 89 pages.

Furness III, "Area Surveillance Systems and Methods," U.S. Appl. No. 61/597,586, filed Feb. 10, 2012, 72 pages.

Furness, III et al., "Method, Apparatus, and Article to Facilitate Evaluation of Objects Using Electromagnetic Energy," U.S. Appl. No. 60/871,639, filed Dec. 22, 2006, 140 pages.

Furness, III et al., "Method, Apparatus, and Article to Facilitate Evaluation of Objects Using Electromagnetic Energy," U.S. Appl. No. 60/883,312, filed Jan. 3, 2007, 147 pages.

Furness, III et al., "Method, Apparatus, and Article to Facilitate Evaluation of Objects Using Electromagnetic Energy," U.S. Appl. No. 60/890,446, filed Feb. 16, 2007, 155 pages.

Furness, III et al., "Methods, Apparatus, and Article to Facilitate Evaluation of Objects Using Electromagnetic Energy," U.S. Appl. No. 60/834,589, filed Jul. 31, 2006, 135 pages.

International Search Report, mailed Jun. 21, 2007, for PCT/US2005/039495, 1 page.

International Search Report, mailed Jul. 23, 2008, for PCT/US2007/017082, 1 page.

International Search Report, mailed Feb. 25, 2013, for PCT/US2012/056135, 3 pages.

International Search Report, mailed May 15, 2013, for PCT/US2013/025162, 3 pages.

International Search Report, mailed May 13, 2013, for PCT/US2013/025164, 3 pages.

(56) References Cited

OTHER PUBLICATIONS

International Search Report and Written Opinion, mailed Jun. 29, 2014, for PCT/US2014/017776, 11 pages.
Japanese Office Action with English Translation for Corresponding Japanese Patent Application No. 2009-522834, mailed Aug. 7, 2012, 8 pages.
Mander et al., "A Device for Evaluation of Fluids Using Electromagnetic Energy," U.S. Appl. No. 13/797,737, filed Mar. 12, 2013, 61 pages.
Mander et al., "A Device for Evaluation of Fluids Using Electromagnetic Energy," U.S. Appl. No. 61/767,716, filed Feb. 21, 2013, 61 pages.
Mander et al., "Method, Apparatus, and Article to Facilitate Evaluation of Substances Using Electromagnetic Energy," U.S. Appl. No. 13/796,835, filed Mar. 12, 2013, 74 pages.
Mander et al., "Method, Apparatus, and Article to Facilitate Evaluation of Substances Using Electromagnetic Energy," U.S. Appl. No. 61/760,527, filed Feb. 4, 2013, 72 pages.
Mander et al., "Systems and Methods for Fluid Analysis Using Electromagnetic Energy," U.S. Appl. No. 61/777,750, filed Mar. 12, 2013, 39 pages.
Purdy, "Fluid Medium Sensor System and Method," U.S. Appl. No. 61/538,617, filed Sep. 23, 2011, 75 pages.
Schowengerdt et al., "Method, Apparatus, and Article to Facilitate Distributed Evaluation of Objects Using Electromagnetic Energy," U.S. Appl. No. 60/834,662, filed Jul. 31, 2006, 96 pages.
Schowengerdt et al., "System and Method of Evaluating an Object Using Electromagnetic Energy," U.S. Appl. No. 60/820,938, filed Jul. 31, 2006, 69 pages.
Schowengerdt, "Brief Technical Description of the Cyclops Spectral Analysis and Authentication System," Visualant Inc. memorandum, not disclosed prior to Dec. 22, 2006, 2 pages.
Thomas, "A Beginner's Guide to ICP-MS—Part V: The Ion Focusing System," *Spectroscopy* 16(9):38-44, Sep. 2001.
Turpin et al., "Full Color Spectrum Object Authentication Methods and Systems," U.S. Appl. No. 60/732,163, filed Oct. 31, 2005, 198 pages.
Turpin, "Full Color Spectrum Object Authentication Methods and Systems," U.S. Appl. No. 60/623,881, filed Nov. 1, 2004, 114 pages.
Vrhel, "An LED based spectrophotometric instrument," *Color Imaging: Device-Independent Color, Color Hardcopy, and Graphic Arts IV, Proceedings of the SPIE* 3648:226-236, Jan. 1999.
Written Opinion, mailed Jun. 21, 2007, for PCT/US2005/039495, 5 pages.
Written Opinion, mailed Jul. 23, 2008, for PCT/US2007/017082, 3 pages.
Written Opinion, mailed Feb. 25, 2013, for PCT/US2012/056135, 4 pages.
Written Opinion, mailed May 15, 2013, for PCT/US2013/025162, 7 pages.
Written Opinion, mailed May 13, 2013, for PCT/US2013/025164, 6 pages.
International Search Report and Written Opinion, mailed Sep. 4, 2014, for International Application No. PCT/US2014/024100, 9 pages.
International Search Report and Written Opinion of the International Searching Authority, mailed Dec. 8, 2014 for corresponding International Application No. PCT/US14/14656, 12 pages.
International Search Report and Written Opinion of the International Searching Authority, mailed Sep. 4, 2014 for corresponding International Application No. PCT/US2014/024100, 7 pages.
V-Led, "Product Information—9900-1201-13," 2006, retrieved from http://www.v-led.com/pages/products/9900__1201__13.html on Aug. 22, 2016, 5 pages.

* cited by examiner

SYSTEMS FOR FLUID ANALYSIS USING ELECTROMAGNETIC ENERGY THAT IS REFLECTED A NUMBER OF TIMES THROUGH A FLUID CONTAINED WITHIN A REFLECTIVE CHAMBER

BACKGROUND

Technical Field

The present disclosure generally relates to analytical devices and, in particular, analytical devices that employ electromagnetic energy (e.g., optical wavelengths such as near-infrared through near-ultraviolet) to analyze fluids (e.g., gases).

Description of the Related Art

There are a large number of applications in which it is useful to analyze a fluid, for instance, a gas or composition of gases. Such may include identifying the component or components of the fluid, which may or may not include contaminants. Such may also include determining relative concentrations of components of the fluid.

A relatively simple and inexpensive system to analyze fluids is desirable.

BRIEF SUMMARY

Systems for analyzing fluids (e.g., gases) include a chamber structure with a reflective inner surface, emitters, a primary detector positioned to principally detect electromagnetic energy reflected numerous times through the gas (es) and a calibration detector positioned to detect electromagnetic energy not reflected numerous times through the gas(es). Calibration may be automatically performed. The primary detector relies principally on Raleigh scattering. An optional primary detector may be positioned to principally detect Raman scattered electromagnetic energy.

A sampling system may be summarized as including an elongated chamber structure to hold a fluid to be sampled, the elongated chamber structure having at least one wall that at least partially separates an interior of the chamber structure from an exterior thereof, the chamber structure having a first end and a second end, the second end opposite from the first end along a length of the chamber structure, at least a first portion of the elongated chamber structure reflective at least laterally across the interior of the chamber structure along at least a first portion of the length of the chamber structure; a set of emitters positioned to emit electromagnetic energy into the interior of the chamber structure proximate the first end laterally across the interior of the chamber structure, and at an angle extending toward the second end from the first end; at least one primary lateral sampling detector positioned to detect electromagnetic energy from the interior of the chamber structure proximate the second end of the chamber structure and laterally with respect to the length of the chamber structure; and at least one calibration detector positioned to detect electromagnetic energy from the interior of the chamber structure proximate the first end of the chamber structure and spaced relatively toward the second end with respect to the set of emitters.

The set of emitters may be positioned to emit electromagnetic energy into the interior of the chamber structure at an angle extending toward the second end from at least proximate the first end of the chamber structure. The angle may be a user selectively adjustable angle. The angle may be selectively adjustable to achieve a defined at least minimum number of reflections of electromagnetic energy laterally across the interior of the chamber structure as the electromagnetic energy passes from the set of emitters to the at least one primary lateral sampling detector. The defined at least minimum number of reflections of electromagnetic energy may be greater than a number of reflections of the electromagnetic energy laterally across the interior of the chamber structure as the electromagnetic energy passes from the set of emitters to the at least one calibration detector. The defined at least minimum number of reflections of electromagnetic energy may be at least ten times greater than a number of reflections of the electromagnetic energy laterally across the interior of the chamber structure as the electromagnetic energy passes from the set of emitters to the at least one calibration detector. The set of emitters may be moveable to emit electromagnetic energy into the interior of the chamber structure at a user selectively adjustable angle extending toward the second end from at least proximate the first end of the chamber structure. The set of emitters may be pivotally mounted for rotation with respect to the interior of the chamber structure at a user selectively adjustable angle extending toward the second end from at least proximate the first end of the chamber structure. The at least one primary lateral sampling detector may include a photodiode response to at least some near-infrared wavelengths of the electromagnetic energy through at least some near-ultraviolet wavelengths of the electromagnetic energy. The at least one primary lateral sampling detector may include at least one photodiode.

The sampling system may further include at least one primary axial sampling detector positioned to detect electromagnetic energy from the interior of the chamber structure proximate the second end of the chamber structure, axially along the length of the chamber structure.

At least a second portion of the elongated chamber structure may be non-reflective at least laterally across the interior of the chamber structure along at least a second portion of the length of the chamber structure immediately preceding the at least one primary axial sampling detector.

The sampling system may further include a shroud having a proximal end and a distal end, the shroud extending at the proximate end thereof from the second end of the chamber structure, the shroud having an interior wall that is nonreflective, and wherein the at least one primary axial sampling detector is positioned at least proximate the distal end of the shroud.

The at least one primary axial sampling detector may include at least one a complementary metal oxide semiconductor (CMOS) detector, a charged coupled detector (CCD) detector, or a two-dimensional image detector.

The sampling system may further include at least one port to selectively provide fluid communicative coupling between the interior and the exterior of the chamber structure.

The interior of the chamber structure may be selectively sealable at pressures greater than one atmospheres. The interior of the chamber structure may be selectively sealable at pressures greater than X atmospheres.

A sampling system for sampling pressurized gases may be summarized as including an elongated tubular structure having a first end, a second end, a principal axis extending between the first and the second ends, an interior surface that forms an interior to hold pressurized gases to be sampled, at least a portion of the interior surface of the tubular structure optically reflective at least laterally across the principal axis along at least a first portion of a length of the tubular structure; a plurality of emitters operable to provide electromagnetic energy in the interior of the tubular structure at least proximate the first end and directed at least partially laterally across the interior of the tubular structure at an angle to the principal axis that extends toward the second end, each of the emitters selectively operable to emit electromagnetic energy in a respective range of wavelengths in an optical portion of the electromagnetic spectrum, the ranges of wavelengths of at least some of the emitters different from the ranges of wavelengths of others of the emitters; at least one primary lateral sampling detector positioned laterally of the principal axis to detect primarily Rayleigh scattered electromagnetic energy from the pressurized gases to be sampled proximate the second end of the chamber structure; and at least one primary axial sampling detector positioned axially to the principal axis to detect primarily Ramen scattered electromagnetic energy from the pressurized gas to be sampled proximate the second end of the chamber structure; and at least one calibration detector positioned laterally of the principal axis to detect primarily Rayleigh scattered electromagnetic energy from the pressurized gases to be sampled proximate the first end of the chamber structure.

The at least one primary lateral sampling detector may include at least one photodiode, and the at least one primary axial sampling detector may include at least one a complementary metal oxide semiconductor (CMOS) detector, a charged coupled detector (CCD) detector, or a two-dimensional image detector. The at least one calibration detector may include at least one photodiode. The angle at which the emitters emit may be selectively adjustable. The emitters may be pivotally mounted for rotation together with respect to the interior of the tubular structure to selectively adjust the angle at which the emitters emit. The tubular structure may have a rectangular or conic cross-sectional profile perpendicular to the length thereof.

DETAILED DESCRIPTION

Figure 1:
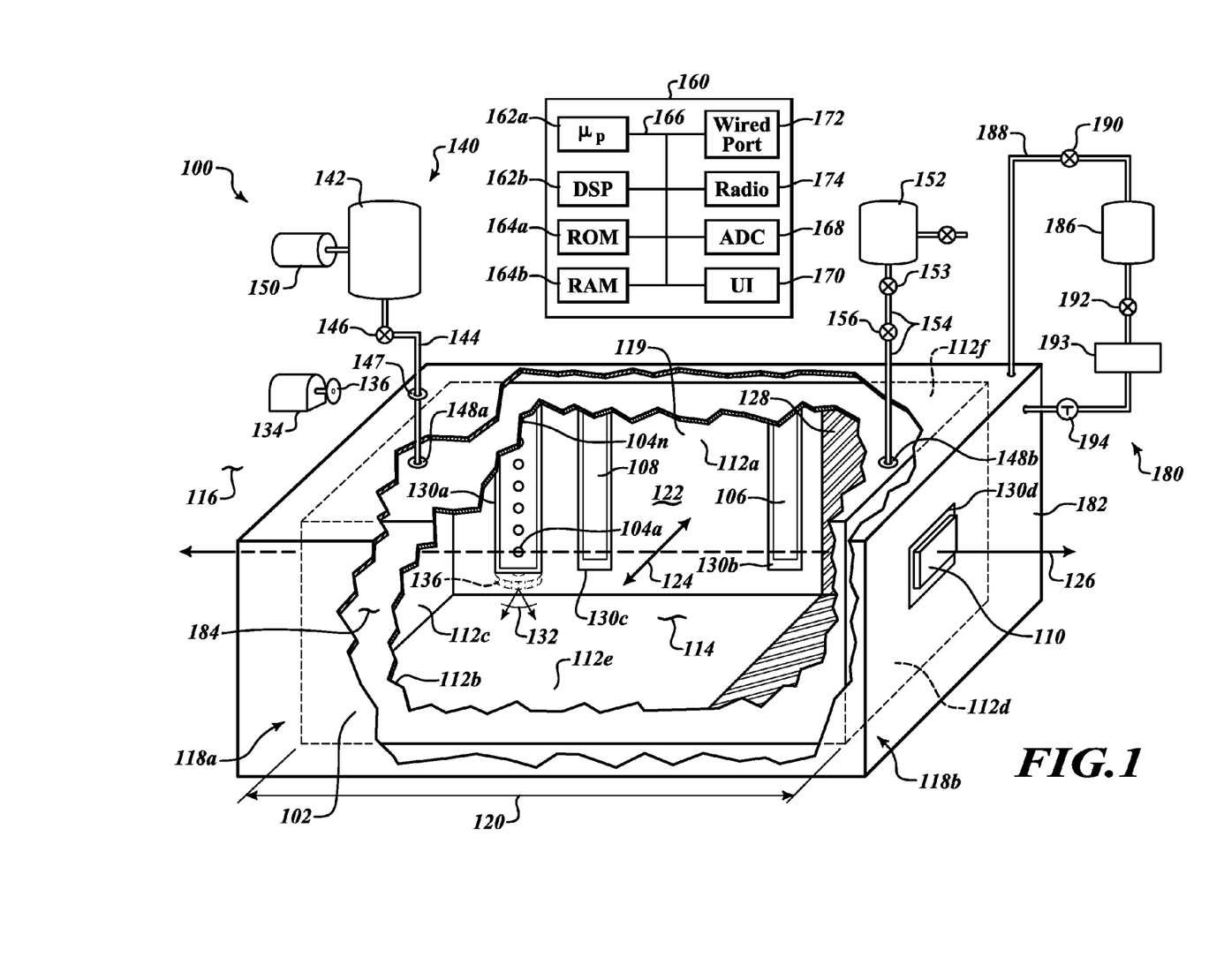
FIG. 1 is an isometric partially broken view of a sampling system for sampling fluids (e.g., gases), according to one illustrated embodiment, including a chamber structure, a number of transducers including emitters that emit electromagnetic energy, a primary lateral sampling detector, a calibration detector, and an optional primary axial sampling detector.

FIG. 1 shows a sampling system 100, according to one illustrated embodiment.

The sampling system 100 may be used to sample fluids, for example, gases. The sampling system 100 may be used to determine the constituent components of a fluid, detect contaminants or absence of contaminants, and/or determine relative amounts of gases and/or contaminants. For instance, the sampling system 100 may detect a presence, and optionally a concentration, of various refrigerants in a vapor state, with or without contaminants.

The sampling system 100 includes a chamber structure 102 which receives a fluid to be sampled and a number of transducers to actively sample the fluid using electromagnetic energy (e.g., optical wavelengths extending from near-infrared to near-ultraviolet, inclusive). The transducers may include a plurality or set of emitters 104a-104n (collectively 104) operable to emit electromagnetic energy, at least one primary lateral sampling detector 106, and at least one calibration detector 108. The transducers may optionally include at least one primary axial sampling detector 110.

The chamber structure 102 may be elongated, having at least one wall (collectively 112) that at least partially separates an interior 114 of the chamber structure 102 from an exterior 116 thereof. The chamber structure 102 illustrated in FIG. 1 has six walls 112a-112f, and a generally rectangular cross-sectional profile perpendicular to a length thereof. The chamber structure 102 has a first end 118a and a second end 118b opposite from the first end 118a along the length 120 of the chamber structure 102. At least a portion of an inner surface 122 of the chamber structure 102 is substantially reflective of electromagnetic energy along at least a first portion of the chamber structure 102. In particular, a first portion 119 of the inner surface 122 is reflective laterally (double headed arrow 124) across the interior 114 of the chamber structure 102 along at least a first portion of the length 120 or a principal or central axis 126 of the chamber structure 102.

For example, inner surfaces 122 of the chamber structure 102 may be optically substantially reflective, for instance, having, carrying or bearing an optically reflective material, layer or coating. Aluminum, for example sputtered aluminum may be suitable, particularly if polished to a fine quality. The aluminum may be protected with a suitable coating or layer, for example a layer of silicon oxide which will oxidize to silicon dioxide. For instance, a first pair of laterally opposed walls (e.g., vertical walls 112a, 112b as illustrated in FIG. 1) may have, carry or bear an optically reflective material, layer or coating. A pair of axially or longitudinally end walls 112c, 112d may not be reflective, for instance, omitting any optically reflective material, layer or coating. An second pair of laterally opposed walls (e.g., horizontal top and bottom walls 112e, 112f as illustrated in FIG. 1) may or may not have, carry or bear an optically reflective material, layer or coating.

For example, a portion of the inner surfaces 122 of the chamber structure 102 may be optically non-reflective, for instance having, carrying or bearing an optically non-reflective material, layer or coating. Suitable material may, for example include black optical coating commerically available from Actar Advanced Coatings. For instance, a portion 128 (indicated by cross-hatching) of the first pair of laterally opposed walls (e.g., vertical walls 112a, 112b as illustrated in FIG. 1) spaced between the second window and the second end of the chamber structure may have, carry or bear an optically substantially non-reflective material, layer or coating. The optically substantially non-reflective material, layer or coating may, for example, be black in color. Optionally, as illustrated in FIG. 1, the second pair of laterally opposed walls (e.g., horizontal top and bottom walls 112e, 112f as illustrated in FIG. 1) carry or bear an optically substantially non-reflective material (indicated by cross-hatching), layer or coating, or are composed of such.

The chamber structure 102 includes at least three windows or openings (i.e., optical ports) 130a, 130b, 130c, 130d (four shown, collectively 130) spaced along at least a portion of the length 120 of the chamber structure 102, and laterally aligned with respect to the principal axis 126 (e.g., longitudinal axis, central axis) or length of the chamber structure. The windows or openings 130 allow optical coupling between the transducers and the gases in the interior 114 of the chamber structure 102.

A first window or opening 130a is positioned proximate the first end 118a and a second window or opening 130b is positioned proximate the second end 118b. A third window or opening 130c is positioned proximate the first end 118a, but spaced relatively toward the second end 118b with respect to the first window 130a. An optional fourth window or opening 130d is positioned at least proximate the second end 118b, axially aligned with respect to the principal axis 126 of the chamber structure 102.

The plurality or set of emitters 104 are operable to emit electromagnetic energy. Each of the emitters 104 is selectively operable to emit electromagnetic energy in a respective range of wavelengths in an optical portion of the electromagnetic spectrum. The ranges of wavelengths of at least some of the emitters 104 different from the ranges of wavelengths of others of the emitters 104. The plurality or set of emitters 104 are aligned with the first window or opening 130a to provide electromagnetic energy in the interior 114 of the chamber structure 102 at least proximate the first end 118a and directed at least partially laterally 124 across the interior 114 of the chamber structure 102 at an angle to the principal axis 126 that extends toward the second end 118b from the first end 118a.

As illustrated in FIG. 1, an angle 130 at which the emitters 104 emit is selectively adjustable. For example, the emitters 104 may be pivotally mounted for rotation with respect to the interior of the chamber structure 102 or the principal axis 126 to selectively adjust the angle 130 at which the emitters 104 provide electromagnetic energy to the interior 114 of the chamber structure 102. The emitters 104 may, for instance, be pivotally mounted to a structure 132 for rotation together, as a unit, group or set. The emitters 104 may be manually rotated or may be rotated by an actuator 134 (e.g., electric motor, solenoid, shape memory alloy, piezoelectric crystal, spring) via a drive train 136 (e.g., gears, rack and pinion, drive belt, linkage). Pivotally mounting the emitters 104 allows adjustment of the angle of incidence of the emitters to the reflective wall 112a. This allows control over the number of reflections of light from reflective wall to reflective wall 112a, 112b, and hence the number of passes through the gas(es) in the chamber structure 102.

At least one primary lateral sampling detector 106 is aligned with the second window or opening 130b. The at least one primary lateral sampling detector 106 is positioned laterally of the principal axis 126 to detect primarily Rayleigh scattered electromagnetic energy from the gases to be sampled proximate the second end 118b of the chamber structure 102. The at least one primary lateral sampling detector 106 detects an intensity of scattered light, independent of wavelength. One or more photodiodes may be suitable for use as the at least one primary lateral sampling detector 106. The photodiode(s) may take the form of a two-dimensional or area photodiode, of sufficient dimensions to detect across substantially the entire height of the interior 114 of the chamber structure 102. Standard commerically available photodiodes (e.g., germanium photodiodes and/or silicon photodiodes) may be employed.

At least one calibration detector 108 is aligned with the third window or opening 130c. The at least one calibration detector 108 is positioned laterally 124 of the principal axis 126 to detect primarily Rayleigh scattered electromagnetic energy from the gases to be sampled proximate the first end 118a of the chamber structure 102. While proximate the first end 118a, the calibration detection 108 is positioned slightly toward the second end 118b with respect to the emitters 104. The at least one calibration detector 108 detects an intensity of scattered light, independent of wavelength. One or more photodiodes may be suitable for use as the at least one calibration detector 108. The photodiode(s) may take the form of a two-dimensional or area photodiode, of sufficient dimensions to detect across substantially the entire height of the interior 114 of the chamber structure 102. Standard commerically available photodiodes (e.g., germanium photodiodes and/or silicon photodiodes) may be employed.

Optionally, at least one primary axial sampling detector 110 is aligned with the optional fourth window or opening 130d. The at least one primary axial sampling detector 110 is positioned axially 124 aligned with a principal axis 126 to detect primarily Raman scattered electromagnetic energy from the gases to be sampled proximate the second end 118b of the chamber structure 102. The at least one primary axial sampling detector 110 detects or is responsive to spectral content or wavelength. One or more complementary metal oxide semiconductor (CMOS) detectors, charged coupled detectors (CCDs) or similar wavelength responsive detectors may be suitable as the at least one primary axial sampling detector 110. A suitable detector may take the form of a pyroelectric detector commercially available from Pyreos Ltd.

The primary lateral sampling detector 106 is positioned to detect off axis (i.e., lateral) scattering, while the primary axial sampling detector 110 is positioned to detect Raman scattering. Since in some instances the Raman scattering may be very small compared with the off axis scattering, a transmission filter may be employed positioned toward the second end 118*b* before the primary axial sampling detector 110, and before any separate sensors (not illustrated) employed to detect scattering or fluorescent emission, if any.

While an exemplary positioning of the emitters 104, primary lateral sampling detector 106, calibration detector 108 and primary axial sampling detector 110 is shown, other positioning of emitters 104 and/or detectors 106, 108, 110 may be employed. For example, the use of various optical elements (e.g., lenses, mirrors, reflectors, prisms) may allow the emitters 104, primary lateral sampling detector 106, calibration detector 108 and/or primary axial sampling detector 110 to be positioned or arranged in other locations or other arrangements, while still providing electromagnetic energy proximate one end (e.g., first end 118*a*), detecting calibration samples of electromagnetic energy before such electromagnetic energy has traversed any appreciable length along the length 120 of the chamber structure 102, and detecting primary lateral samples of electromagnetic energy after such has traversed an appreciable portion along the length 120 of the chamber structure 102.

The chamber structure 102 may be capable of holding fluids at an elevated pressure, that is above one atmosphere. Additionally, the chamber structure may be capable of holding fluids at or at least proximate defined temperatures. Maintaining a fluid such as a gas in the chamber structure 102 under pressure and at defined temperatures may ensure that there are sufficient numbers of molecules to allow accurate detection of the component(s) or constituent(s) using electromagnetic energy. A fluid supply subsystem 140 may be employed to pressurize fluid in the interior 114 of the chamber structure 102.

The fluid supply subsystem 140 may include a supply reservoir 142 which may supply the fluid to the interior 114 of the chamber structure 102 via conduit(s) 144, valve(s) 146 and port(s) 148*a*. A compressor 150 or other device may be fluidly communicatively coupled to ensure that the fluid is maintained at a specified or nominal pressure. While illustrated coupled to the supply reservoir 142, the compressor 150 may be fluidly communicatively coupled directly to the interior 114 of the chamber structure 102 in some implementations. One or more pressure and/or temperature sensors or transducers 147 may provide signals indicative of pressure and/or temperature, as part of a feedback system (not shown) to maintain the fluid at the specified or nominal pressure and/or temperature.

The fluid supply subsystem 140 and/or the chamber structure 102 itself may include or be thermal coupled to a temperature control subsystem 180. The temperature control subsystem 180 may for example, include a jacket 182 that provides a fluidly communicative path 184 between the jacket 182 and at least a portion of a wall of the chamber structure 102. The temperature control subsystem 180 flows a thermal transfer medium through the fluidly communicative path 184 to conductive transfer heat to or away from the contents of the chamber structure 102. The thermal transfer medium will typically have a relatively high capacity for conducting heat. The jacket 182 may be positioned to an outside or exterior of the chamber structure 102, as illustrated in FIG. 1. Alternatively, the jacket 182 may be positioned to an inside or interior of the chamber structure 102. As another alternative the jacket 182 may be coupled to a thermal transfer medium supply reservoir 186. As yet a further alternative a heater or cooler may be thermally coupled with either the chamber structure 102, contents of the chamber structure 102, and/or the thermal transfer medium supply reservoir 1186 or the contents of the thermal transfer medium reservoir 186. For example, the temperature control subsystem 180 may employ one or more resistive heaters, Peltier devices or other devices, collectively 196 suitable for heating or cooling as needed. The temperature control subsystem 180 may include one or more conduits 188, pumps 190, and/or valves 192 to provide fluid transfer medium to and from the jacket 182. The temperature control subsystem 180 may include one or more sensors or transducers 194 (e.g., thermocouples) to provide feedback in the forms of signals indicative of temperature. The temperature control subsystem 180 may employ the feedback to control one or more heaters or coolers 193 to maintain the contents of the chamber structure 102 of the at a desired temperature. Such may include heating and/or cooling the contents. Temperature control may be combined or integrated with the pressure control given the relationship between pressure and temperature. Thus, a desired pressure may be maintained at a desired temperature, enhancing the reliability of the system. The pressure and temperature sensors or transducers 147, 194 may be built into the system, and protected from the fluids, contaminants and any substances used to clean the interior of the chamber structure 102.

A collection reservoir 152 may collect the fluid from the interior 114 of the chamber structure 102 via conduit(s) 154, valve(s) 156 and port(s) 148*b*. A vacuum pump 153 may be fluidly communicatively coupled to an interior 114 of the chamber structure 102, and operable to create an at least partial vacuum in the interior 114. As explained below, the vacuum pump 153 may be used to evacuate previously tested gas(es) from the interior 114 of the chamber structure 102. In some implementations, a single reservoir may be employed to both supply and collect the fluid.

Fluids may be supplied and/or collected in batches in a batch mode of operation. Thus, fluids would be supplied to and retained in the interior 114 of the chamber structure 102 until sampling were complete. Fluids would then be expelled from the interior 114 of the chamber structure 102, and another batch of fluid(s) supplied. Alternatively, fluids may be supplied to and/or collected from the interior 114 of the chamber structure 102 as a continuous flow in a continuous mode of operation. Thus, fluids would be continually supplied during sampling, for example, flowing from one end (e.g., first end 118*a*) of the chamber structure 102 to another end (e.g., second end 118*b*).

The sampling system 100 may include a control subsystem 160. The control subsystem 160 may take an of a large variety of forms, one of which is illustrated in FIG. 1.

The control subsystem 160 is communicatively coupled to control the emitters 104. The control subsystem 160 is communicatively coupled to receive signals from, and optionally control, the primary lateral sampling detector 106, calibration detector 108 and primary axial sampling detector 110.

The control subsystem 160 may include one or more controllers (collectively 162). The controller(s) 162 may, for example, take the form of an integrated circuit package that includes one or more microprocessors 162*a*, digital signal processors (DSPs) 162*b*, application specific integrated circuits (ASICs), programmable gate arrays (PGAs), programmable logic controllers (PLCs), or other logic executing device, denominated herein as a central processing unit. In some implementations, the microprocessor(s) 162a are employed to control the sampling system 100, for instance, activating the emitters 104 and/or the actuator 134. The DSPs 162b may be employed to process and analyze signals and information collected via the various sensors or detectors (e.g., primary lateral sampling detector 106, calibration detector 108 and primary axial sampling detector 110).

The control subsystem 160 may include one or more non-transitory computer- or processor-readable media (collectively 164), for example, one or more memories such as read only memory (ROM) or Flash memory 164a and random access memory (RAM) 164b. While the ROM or Flash memory 164a and RAM 164b are shown separately, such may be integrated into the same integrated circuit (ICs) package as the controller(s) 162 for instance, as discrete IC.

One or more buses 166 may couple the ROM 164a and RAM 164b to the controller(s) 162. The buses 166 may take a variety of forms including an instruction bus, data bus, other communications bus and/or power bus. The nonvolatile ROM and/or Flash memory 164a may store instructions and/or data for controlling the sampling device 100. The volatile RAM 164b may store instructions and/or data for use during operation of the sampling device 100.

The control subsystem 160 may, for example, include an analog-to-digital converter 168, communicatively coupled to convert analog signals, for instance, from the sensor, to digital signals for use by the controller 162. The control subsystem 160 may, for example, include a level translator (not shown) coupled to translate signal levels. The control subsystem 160 may, for example, include a current source (not shown), to supply a constant current to the other components, for instance, emitters 104 such as LEDs or laser diodes. The control subsystem 160 may, for example, include an oscillator or clock, for instance, a crystal oscillator (not shown), communicatively coupled to the controller(s) 162 to provide a clock signal thereto. The control subsystem 160 may, for example, include one or more capacitors, for instance, a tantalum capacitor (not shown).

The controller 162 employs instructions and or data from the ROM/Flash 164a and RAM 164b in controlling operation of the sampling device 100. For example, the controller 162 operates the emitters 104 in one or more sequences. The sequences determine an order in which the emitters 104 are turned ON and OFF. The sequences may also indicate an ordered pattern of drive levels (e.g., current levels, voltage levels, duty cycles) for the emitters 104. Thus, for example, a controller 164 may cause the application of different drive levels to respective ones of the emitters 104 to cause the emitters 104 to emit in distinct bands of the electromagnetic spectrum.

The controller 164 may process information generated by the primary lateral sampling detector 106, calibration detector 108 and primary axial sampling detector 110, which is indicative of the response to illumination by the emitters 104. In the case of the calibration detector 108, the information is indicative of a response by the calibration detector 108 to illumination by the emitters 104 without much influence by a sample or specimen. In the case of the primary lateral sampling detector 106, the information is indicative principally or substantially of a response by a sample or specimen to illumination by the emitters 104 and resultant Rayleigh scattering. In the case of the primary axial sampling detector 110, the information is indicative principally or substantially of a response by a sample or specimen to illumination by the emitters 104 and resultant Raman scattering of electromagnetic energy (e.g., laser light) by gas(es) being sampled.

The information at any given time may be indicative of the response by the sample or specimen to illumination by one or more of the emitters 104. Thus, the information over a period of time may be indicative of the responses by the sample or specimen to sequential illumination by each of a plurality of the emitters 104, where each of the emission spectra of each of the emitters 104 has a different center, bandwidth and/or other more complex differences in spectral content, such as those described above (e.g., the width of the band, the skew of the distribution, the kurtosis, etc.). As discussed in detail below, the sampling operation may be automatically integrated with a calibration operation.

The control subsystem 160 may optionally include a buffer (not shown) to buffer information received from the primary lateral sampling detector 106, calibration detector 108 and primary axial sampling detector 110. The control subsystem 160 may further optionally include an analog to digital converter (ADC) 168 and/or digital to analog converter (DAC) (not shown). An ADC 168 may, for example, be used for converting analog photodiode responses into digital data for further analysis and/or transmission. A DAC may, for example, be used for converting digital computer or controller commands into analog LED or laser diode current levels. The control subsystem 160 may additionally or alternatively optionally include an analog signal processor, which may be particularly useful where the sensor takes the form of one or more photodiodes.

The pressure and temperature control subsystems, #1 may be responsive to the control subsystem to maintain pressure and temperature within a desired range of specified pressure and temperature values. The control subsystem 160 may include a user interface 170 including one or more user interface devices. For example, the user interface 170 may include one or more speakers or microphones (not shown). Also, for example, the user interface 170 may include one or more visual indicators, such as one or more LEDs, liquid crystal displays (LCD), or other visual indicator. The LCD may, for example, take the form of a touch sensitive LCD, which displays a graphical user interface, operable by the user of the sampling device 100. Additionally, or alternatively, the user interface 170 may include one or more user operable input elements, such as switches, keys or buttons (not shown). The input elements may include a switch for turning the sampling device 100 ON and OFF. Additionally, or alternatively, the input elements may include one or more switches or keys for controlling the operation of the test device 100, for example, downloading or uploading data or instructions to or from the sampling device 100. Such may be via one or more connectors, for instance, a debug connector (not shown) and a programming connector (not shown), both positioned to be accessible from an exterior of the sampling device 100.

The control subsystem 160 may include one or more communications interfaces. The communications interfaces may allow networked communications (e.g., LANs, WANs, WLANs, WWANs, PSTN, ETHERNET, TCP/IP) and non-networked communications (e.g., USB®, Firewire®, Thunderbolt®).

For example, the control subsystem 160 may include one or more wired or optical interfaces, for instance, one or more wired ports 172 (one shown). The wired port and any associated interfaces may, for example, be compatible with various networking protocols.

Also for example, the control subsystem may include one or more wireless ports 174, for example, a radio (i.e., wireless transmitter, receiver, transceiver, antenna). The radio may be compatible with any of a large variety of wireless communications protocols including cellular protocols (e.g., CDMA, GSM®, LTE®) and wireless networking protocols (e.g., BLUETOOTH®, WI-FI®, IEEE 802, 11).

The sampling device 100 may optionally include a power source (not shown). The power source may take the form of a portable power source, for example, one or more batteries, fuel cells, and/or super- or ultra-capacitors. Additionally, or alternatively, the power source may take the form of a fixed power source, such as a cable plugged into a port of a computer (e.g., USB cable) or a conventional electrical receptacle (e.g., wall outlet).

Figure 2A:
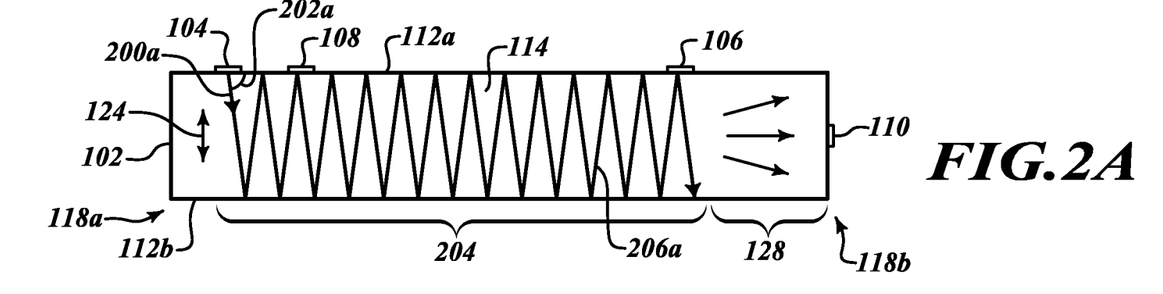
FIG. 2A is a top plan view of the sampling system showing illustrative ray tracing of electromagnetic energy emitted by emitters at a first angle, the electromagnetic energy detected by the primary lateral sampling detector, calibration detector, and optional primary axial sampling detector, according to one illustrated embodiment.
Figure 2B:
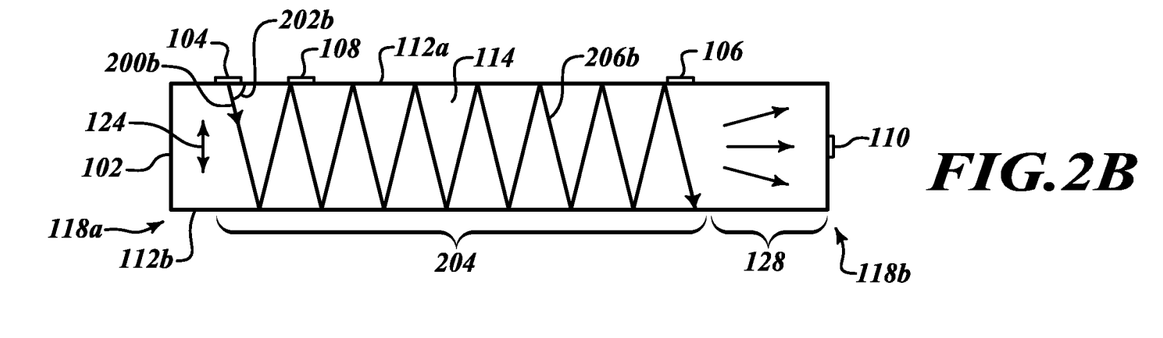
FIG. 2B is a top plan view of the sampling system showing illustrative ray tracing of electromagnetic energy emitted by emitters at a second angle, the electromagnetic energy detected by the primary lateral sampling detector, calibration detector, and optional primary axial sampling detector, according to one illustrated embodiment.

FIGS. 2A and 2B best illustrate operation of the above described arrangement. In particular, FIG. 2A shows emission or delivery of electromagnetic energy 200a at a first angle 202a, while FIG. 2B shows emission or delivery of electromagnetic energy 200b at a second angle 202b different from the first angle 202a.

The interior 114 of the chamber structure 102 is initially evacuated, for example via outlet port 148b (FIG. 1) and vacuum pump 153. The vacuum does not, for course, need to be a complete vacuum, but should be sufficiently low pressure to remove any gas(es) that were previously in the interior 114 of the chamber structure 102. In some applications, residual air may not be objectionable, if such would not adversely affect testing results.

Figure 5:
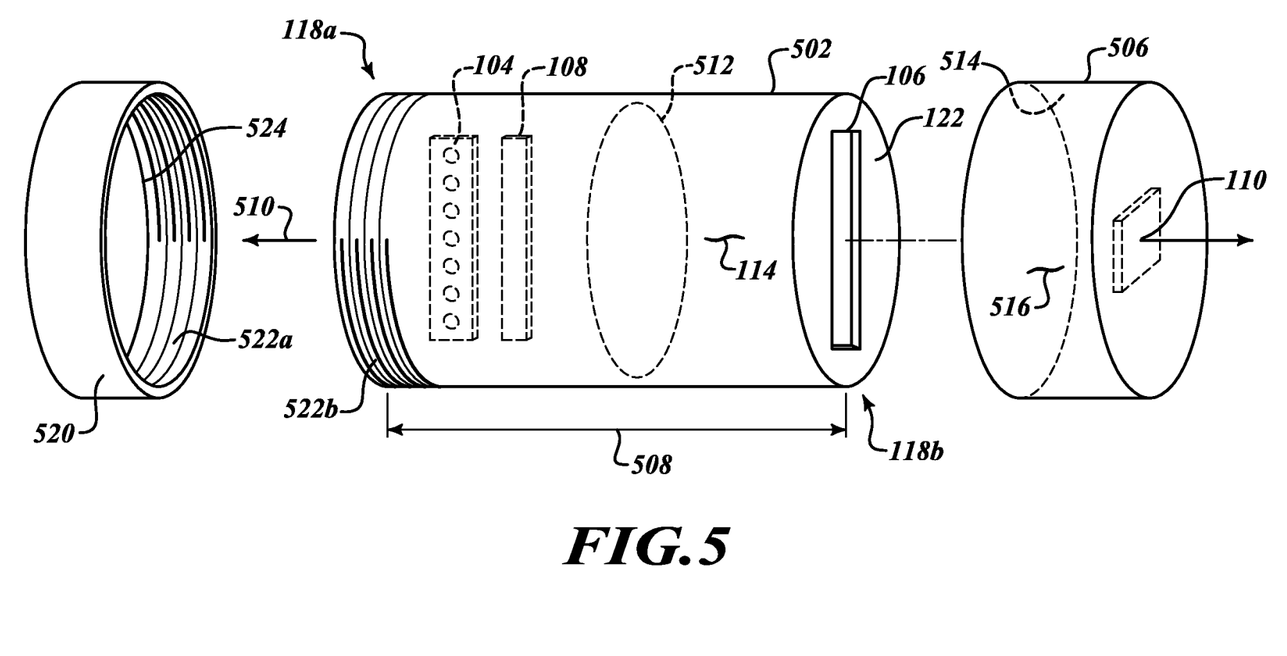
FIG. 5 is an isometric view of a sampling system for sampling fluids (e.g., gases), according to one illustrated embodiment, including a chamber structure having a conical profile or cross-section, a shroud that extends from the sampling chamber, and a number of transducers.

In some applications, the interior 114 of the chamber structure 102 is cleaned to remove any contaminants that may have been in the previously tested gas(es). Cleaning may occur prior to and/or following evacuation via the vacuum. To facilitate cleaning, an end of the chamber structure 102 may be formed as a detachably removable end cap 520 (FIG. 5). The end cap 520 may, for example, be coupled to the chamber structure 102 via a thread (e.g., female thread on interior of end cap) 522a which threadedly engages a complementary thread (e.g., male thread on exterior of chamber structure 102) 522b on the chamber structure 102. The end cap 520 may include an O-ring 524 or similar sealing structure. Once the end cap 520 is removed, the interior 114 of the chamber structure 102 may be scrubbed and/or rinsed. For a cylindrically tubular structure, a bottle brush or similar cleaning tool may be employed. One or more rinses may be used. For instance a detergent rinse to flush oil based contaminants, followed by one or more rinses with fresh water or even deionized water. For such applications it would be beneficial if the various emitters 104, sensors or transducers 106, 108, 110 and/or electronics were protected behind sealed windows, or alternatively removable from the interior 114 of the chamber structure 102 prior to cleaning.

The gas(es) to be sampled or analyzed are then pumped into the interior 114 of the chamber structure 102 via the inlet port 148a (FIG. 1) at a defined or specified pressure and/or temperature. The defined or specified pressure and/or temperature ensures a measurable level of gas concentration. After the interior 114 of the chamber structure 102 contains the pressurized sample gas(es), the gas inlet and outlet ports 148a, 148b are closed.

Individual emitters 104 (e.g., laser diodes) are turned ON sequentially and in various combinations depending upon the type of test (e.g., identity of various gases versus the concentration of various gases). For example, emitters (e.g., four to eight laser diodes with various emission spectra) positioned proximate the first end 118a may direct electromagnetic energy (rays 200a, 200b) laterally across the interior 114 of the chamber structure 102, toward the opposite lateral wall 112b of the chamber structure 102. The reflective portions of the laterally opposed wall(s) 112a, 112b cause repeated lateral reflection, multiple times across the parallel walls 112a, 112b along the length 204 of the chamber structure 102 as illustrated by ray traces 206a, 206b. The total number of reflections per unit of distance traveled along the length 204 is set by the angle 202a, 202b of emission by the emitters 104 with respect to the interior 114 of the chamber structure 102 or principal axis 126 (FIG. 1) thereof.

The reflected electromagnetic energy is first detected by the calibration detector 108, after a relative few reflections. Thus, the electromagnetic energy has passed through the fluid (e.g., gas) relatively few times (e.g., one, two, three), and electromagnetic energy detected by the calibration detector 108 will be relatively unaffected by the fluid. As previously noted, the calibration detector 108 make take the form of a relatively large area photodiode. As also previously noted, the calibration detector 108 is responsive to intensity or magnitude independent of wavelengths. Further, the calibration detector 108 is positioned and oriented to primarily detect Rayleigh scattered electromagnetic energy. The control subsystem 160 uses the readings or measurements of calibration detector 108 to provide a baseline or calibration of the sampling system 100.

The reflected electromagnetic energy is then detected by the primary lateral sampling detector 106, after a relative large number of reflections. Thus, the electromagnetic energy has passed through the fluid (e.g., gas) a relatively large number of times (e.g., ten, twenty, one hundred), and electromagnetic energy detected by the primary lateral sampling detector 106 will be relatively highly affected by the fluid. As previously noted, the primary lateral sampling detector 106 make take the form of a relatively large area photodiode. As also previously noted, the primary lateral sampling detector 106 is responsive to intensity or magnitude independent of wavelengths. Further, the primary lateral sampling detector 106 is positioned and oriented to primarily detect Rayleigh scattered electromagnetic energy. The control subsystem 160 uses the readings or measurements of primary lateral sampling detector 106 to analyze the gas(es), in particular identifying relative concentrations of the constituent components of the gas or other fluid. The control subsystem may adjust the analysis based at least in part on the baseline or calibration.

Finally, the reflected electromagnetic energy is detected by the primary axial sampling detector 110, after a relative large number of reflections. Thus, the electromagnetic energy has passed through the fluid (e.g., gas) a relatively large number of times (e.g., ten, twenty, one hundred), and electromagnetic energy detected by the primary lateral sampling detector 110 will be relatively highly affected by the fluid. As previously noted, the primary axial sampling detector 110 may take the form of a CMOS or CCD detector, and thus is responsive to wavelengths. Further, the primary axial sampling detector 110 is positioned and oriented to primarily detect Raman scattered electromagnetic energy. The control subsystem 160 uses the readings or measurements of primary axial sampling detector 110 to analyze the gas(es), in particular identifying the constituent components and/or presence or absence of a particular gas or contaminant. The control subsystem may adjust the analysis based at least in part on the baseline or calibration.

The readings or measurements by the primary lateral sampling detector 106 and calibration detector 108 by the respective photodiodes may be easily compared. Ideally, depending upon the spectral absorption characteristics of the gases, the relative transmission of light from the individual emitters 104 (e.g., laser diodes) will be used to determine which gases are present and in what concentrations. Emitters 104 (e.g., laser diodes) having respective spectra are selected at least partially based on respective spectra of the spectral absorption data for the gas(es) to be analyzed or sampled. The instrument should be usable for a large variety of gases. Based on a cursory view of the absorption spectra of certain gases used in refrigeration (i.e., refrigerant gasses), suitable spectral emission of the emitters 104 (e.g., laser diodes) may be in the longer IR wavelengths (3-6 microns). The detectors 106, 108 (e.g., photodetectors) should be responsive to at least these longer IR wavelengths (3-6 microns) as well.

As is readily apparent by comparing FIGS. 2A and 2B, in some implementations, the angle 202a, 202b at which the emitters 104 emit is selectively adjustable. For example, the emitters 104 may be pivotally mounted for rotation together as a group with respect to the interior 114 of the chamber structure 102 to selectively adjust the angle 202a, 202b at which the emitters 104 emit or provide electromagnetic energy. The angle 202a, 202b may be selectively adjustable to achieve a defined or specified minimum number of reflections of electromagnetic energy laterally 124 across the interior 114 of the chamber structure 102 as the electromagnetic energy passes from the set of emitters 104 to the at least one primary lateral sampling detector 106. The defined or specified minimum number of reflections of electromagnetic energy may be greater than a total number of reflections of the electromagnetic energy laterally 124 across the interior 114 of the chamber structure 102 as the electromagnetic energy passes from the plurality or set of emitters 104 to the at least one calibration detector 108. The defined or specified minimum number of reflections of electromagnetic energy may, for example, be at least ten times greater than a number of reflections of the electromagnetic energy laterally 124 across the interior 114 of the chamber structure 102 as the electromagnetic energy passes from the set of emitters to the at least one calibration detector 108. For example, an angle approaching 90° with respect to the lateral wall 112b will result in the largest number of reflections per unit length traversed, while an angle approaching 0° will result in the smallest number of reflections per unit length traversed. The structure 136 (FIG. 1) and/or actuator 134 (FIG. 1) may include one or more physical stops or detents to limit the rotation or angle of travel of the emitters 104 between some values greater than 0° and less than 90°. Alternatively, software may impose limits on the rotation or angle of travel of the emitters 104 that limit the selectivity between some values greater than 0° and less than 90°.

Figure 3A:
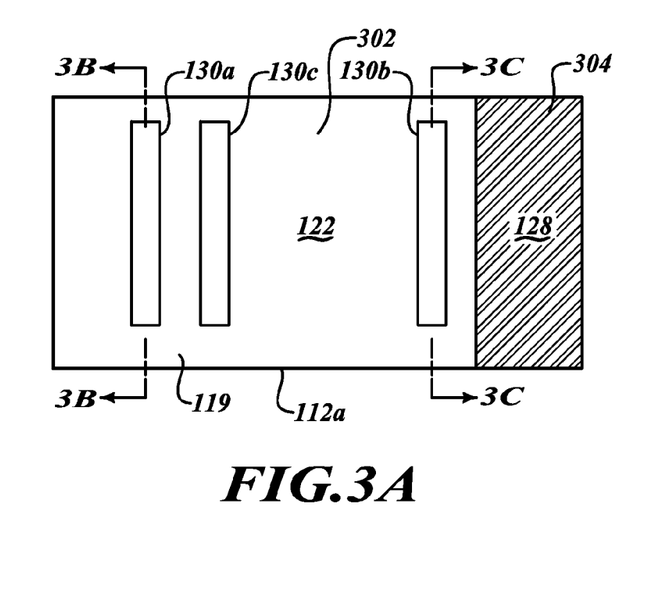
FIG. 3A is a side elevational view of a portion of a sampling system, illustrating a wall with a number of windows formed in a layer thereof, and the emitters carried by a circuit substrate, a primary lateral sampling detector carried by a circuit substrate, and a calibration detector carried by a circuit substrate, according to one illustrated embodiment.
Figure 3B:
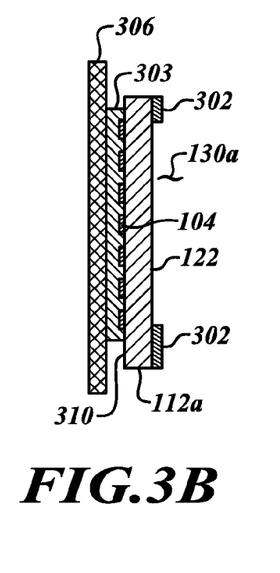
FIG. 3B is a cross-sectional view of the portion of the sampling system of FIG. 3A taken along section line 3B, which includes the emitters and the circuit substrate.
Figure 3C:
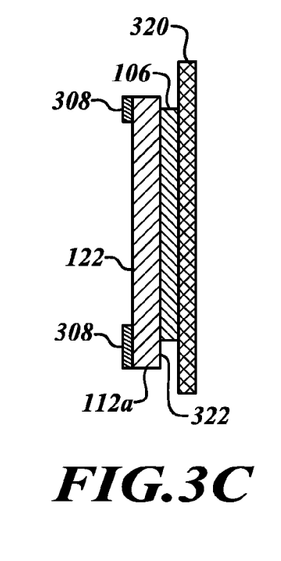
FIG. 3C is a cross-sectional view of the portion of the sampling system of FIG. 3A taken along section line 3C, which includes the primary lateral sampling sensor and the circuit substrate.

FIGS. 3A-3C show one of the lateral walls 112a of the chamber structure 102 along with the emitters 104, primary lateral sampling detector 106 and calibration detector 108, according to one illustrated embodiment.

A first portion 119 of the lateral wall 112a may have a material, layer or coating of an optically substantially reflective material 302 on an inner surface 122. As best illustrated in FIGS. 3B and 3C, the optically substantially reflective material 308 may be omitted or removed (e.g., etched) from select portions of the inner surface 122 to form the windows or openings 130a-130c. A portion 128 of the lateral wall 112a may have a material, layer or coating of an optically substantially non-reflective material 304 on the inner surface 122.

As best illustrated in FIG. 3B, the emitters 104 (only one called out in FIG. 3B) may be carried by a circuit substrate 306, which is aligned with the first window or opening 130a (FIG. 3A). The emitters 104 may be recessed in a layer 308 on the circuit substrate 306 that permits the package to mount flush to an outer surface 306 of the lateral wall 112a. The circuit substrate 302 may be attached by any conventional structure or materials, for example, fasteners, adhesives, or a frame.

As best illustrated in FIG. 3C, the primary lateral sampling detector 106 may be carried by a circuit substrate 320, which is aligned with the second window or opening 130b. The circuit substrate 320 may be the same substrate as the circuit substrate 310, or may be a separate distinct structure. The primary lateral sampling detector 106 mounts flush to an outer surface 322 of the lateral wall 112a. The circuit substrate 320 may be attached by any conventional structure or materials, for example, fasteners, adhesives, or a frame.

Figure 4A:
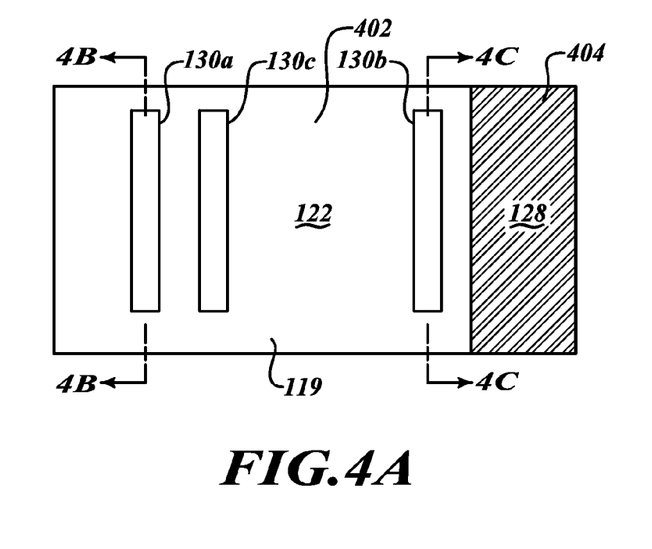
FIG. 4A is a side elevational view of a portion of a sampling system, illustrating a wall with a number of windows or openings formed therein, and the emitters carried by a circuit substrate, a primary lateral sampling detector carried by a circuit substrate, and a calibration detector carried by a circuit substrate, each aligned with a respective window or opening, according to one illustrated embodiment.
Figure 4B:
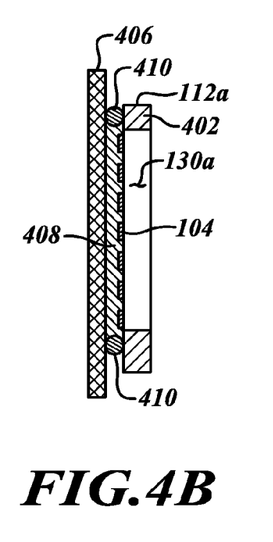
FIG. 4B is a cross-sectional view of the portion of the sampling system of FIG. 4A taken along section line 4B, which includes the emitters and the circuit substrate sealingly coupled about a respective window or opening.
Figure 4C:
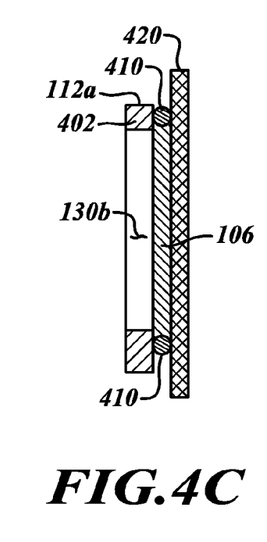
FIG. 4C is a cross-sectional view of the portion of the sampling system of FIG. 4A taken along section line 4C, which includes the primary lateral sampling sensor and the circuit substrate sealingly coupled about a respective window or opening.

FIGS. 4A-4C show one of the lateral walls 112a of the chamber structure 102 along with the emitters 104, primary lateral sampling detector 106 and calibration detector 108, according to one illustrated embodiment.

A first portion 119 of the lateral wall 112a may be composed or comprised of an optically substantially reflective material 402. As best illustrated in FIGS. 4B and 4C, the portion of the lateral wall 112a may be omitted or removed to form the windows, openings, or apertures 130a-130c. A portion 128 of the lateral wall 112a may be devoid of the optically substantially reflective material on the inner surface, or may be covered with an optically substantially non-reflective material 404.

As best illustrated in FIG. 4B, the emitters 104 (only one called out in FIG. 4B) may be carried by a circuit substrate 406, which is aligned with the first window or opening 130a. The emitters 104 may be recessed in a layer 408 on the circuit substrate 406. One or more seals 410 such as a gasket provide sealing engagement about the window, opening or aperture 130a. The circuit substrate 406 may be attached by any conventional structure or materials, for example, fasteners, adhesives or a frame.

As best illustrated in FIG. 4C, the primary lateral sampling detector 106 may be carried by a circuit substrate 420, which is aligned with the second window or opening 130b. The circuit substrate 420 may be the same substrate as the circuit substrate 410, or may be a separate distinct structure. One or more seals 410 such as a gasket provides sealing engagement about the window, opening or aperture. The circuit substrate 420 may be attached by any conventional structure or materials, for example, fasteners, adhesives, or a frame.

FIG. 5 shows a sampling system 500 including a chamber structure 502, shroud 506, along with emitters 104, primary lateral sampling detector 106, calibration detector 108 and optional primary axial sampling detector 110, according to at least one illustrated embodiment.

The chamber structure 502 has a first end 118a, second end 118b and a generally conical cross-sectional profile perpendicular to a length 508 or principal axis 510 of the chamber structure 502. The shroud 506 extends from a second end 118b of the chamber structure 502.

In particular, the chamber structure 502 is illustrated as a cylindrical tubular structure having a circular or oval cross-sectional profile (broken line) 512. The shape or cross-sectional profile of the chamber structure 502 should not be considered limiting. Other shapes, including polygonal shapes, such as hexagonal cross-sectional profiles, may be employed.

The entire inner surface 122 of the chamber structure 502 may be optically reflective, or only a portion thereof may be optically reflective.

The shroud 506 extends from the second end 118b of the chamber structure 502 and has an inner surface 514 that is optically non-reflective. The shroud 506 may be physically coupled to the chamber structure 502 in any of a large variety of ways. For example, the shroud 506 may be press fit to the chamber structure 502, for instance, having an inner dimension sized to securely receive an outer dimension of the chamber structure 502. The particular physical coupling method or structure should not be considered limiting.

In contrast to FIG. 1, the emitters 104, primary lateral sampling detector 106, calibration detector 108 are all received or housed within the interior 114 of the chamber structure 502. Likewise, the primary axial sampling detector 110 may be housed in an interior 516 of the shroud 506. Notably, some implementations may locate some components in the interior 114, 516 of the chamber structure 502 or shroud 506, while other components are located externally from the interior 114, 516 of the chamber structure 502 or shroud 506.

Example

Suitable dimensions of a chamber structure 102, 502 such as that of FIG. 1 may, for example, be approximately 1.5 inches in height, 2.0 inches in width or depth and 6.0 inches in length. Alternatively, suitable dimensions may, for example, be approximately 3 centimeters in height, 8 centimeters in width or depth, and 8 centimeters in length.

A shroud 506 such as that of FIG. 5 may, for example, extend the chamber structure 502 by approximately 1 inch.

Suitable emitters may for example, take the form of shorter wavelength (e.g., in the 300 nm to 1000 nm spectrum) laser diodes, operated to illuminate the interior 114 of the chamber structure 102, 502.

Bandwidth selective filters may be placed over several highly sensitive photodiodes to sense or read out Raman Scattering via a port (in the 900-1600 nm range). Notably, absorption of electromagnetic energy (e.g., light) is measured along a path of the laser beams. In contrast, Raman scattered electromagnetic energy is generally omni-directional, and is sensed or read out at the second end 118b of the chamber structure 102, 502 and not contaminated by the light directly emitted by the emitters 104 (e.g., laser diodes). Raman scattering comes from the relaxation of excited electrons (e.g., raised to higher orbitals by the shorter wavelength electromagnetic energy). Raman scattering may be the best way to identify the specific gases, whereas the light absorption method (e.g. measuring intensity or magnitude) will probably be the best way to quantify the concentration of those gas(es) and/or contaminants.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to: U.S. Pat. Nos. 7,996,173; 8,081,304; and 8,076,630; U.S. Provisional Patent Application Ser. Nos. 60/623,881, filed Nov. 1, 2004; 60/732,163, filed Oct. 31, 2005; 60/820,938, filed Jul. 31, 2006; 60/834,662, filed Jul. 31, 2006; 60/834,589, filed Jul. 31, 2006; 60/871,639, filed Dec. 22, 2006; 60/883,312, filed Jan. 3, 2007; 60/890,446, filed Feb. 16, 2007; 61/538,617, filed Sep. 23, 2011; 61/597,586, filed Feb. 10, 2012; 61/597,593, filed Feb. 10, 2012; 61/760,527, filed Feb. 4, 2013; 61/767,716, filed Feb. 21, 2013; and 61/777,750, filed Mar. 12, 2013 are incorporated herein by reference, in their entirety. Aspects of the embodiments can be modified, if necessary, to employ systems, circuits and concepts of the various patents, applications and publications to provide yet further embodiments.

In some implantations, it may be advantageous to couple one end of the chamber structure 102 to another tube, which supplies gases to the interior of the chamber structure 102. Such may implement a continuous flow analysis system, or at least facilitate automation of a batch flow system. One or more mass flow sensors or transducers may be located in the fluid flow path to quantize the amounts of gases being tested or analyzed.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sampling system, comprising:
an elongated chamber structure to hold a fluid to be sampled, the elongated chamber structure having at least one wall that at least partially separates an interior of the chamber structure from an exterior thereof, the chamber structure having a first end and a second end, the second end opposite from the first end along a length of the chamber structure that extends along a principal axis of the chamber structure, at least a first portion of the elongated chamber structure reflective at least laterally across the interior of the chamber structure along at least a first portion of the length of the chamber structure;
a set of emitters positioned to emit electromagnetic energy into the interior of the chamber structure proximate the first end laterally across the interior of the chamber structure, and at an angle extending toward the second end from the first end;
at least one primary lateral sampling detector proximate the second end of the chamber structure and positioned laterally with respect to the principal axis of the chamber structure to detect electromagnetic energy from the interior of the chamber structure proximate the second end of the chamber structure;
at least one calibration detector proximate the first end of the chamber structure with respect to the at least one primary lateral sampling detector and spaced relatively toward the second end with respect to the set of emitters, the at least one calibration detector positioned laterally with respect to the principal axis of the chamber structure to detect electromagnetic energy from the interior of the chamber proximate the first end of the chamber structure; and
at least one primary axial sampling detector proximate the second end of the chamber structure and positioned axially along the principal axis of the chamber structure to detect electromagnetic energy from the interior of the chamber structure proximate the second end of the chamber structure.

2. The sampling system of claim 1 wherein the first distance is longer than the second distance.

3. The sampling system of claim 2 wherein the angle is a user selectively adjustable angle.

4. The sampling system of claim 2 wherein the angle is selectively adjustable to achieve a defined at least minimum number of reflections of electromagnetic energy laterally across the interior of the chamber structure as the electromagnetic energy passes from the set of emitters to the at least one primary lateral sampling detector.

5. The sampling system of claim 4 wherein the defined at least minimum number of reflections of electromagnetic energy is greater than a number of reflections of the electromagnetic energy laterally across the interior of the chamber structure as the electromagnetic energy passes from the set of emitters to the at least one calibration detector.

6. The sampling system of claim 4 wherein the defined at least minimum number of reflections of electromagnetic energy is at least ten times greater than a number of reflections of the electromagnetic energy laterally across the interior of the chamber structure as the electromagnetic energy passes from the set of emitters to the at least one calibration detector.

7. The sampling system of claim 1 wherein the set of emitters are moveable to emit electromagnetic energy into the interior of the chamber structure at a user selectively adjustable angle extending toward the second end from at least proximate the first end of the chamber structure.

8. The sampling system of claim 1 wherein the set of emitters are pivotally mounted for rotation with respect to the interior of the chamber structure at a user selectively adjustable angle extending toward the second end from at least proximate the first end of the chamber structure.

9. The sampling system of claim 1 wherein a ratio of distance between the set of emitters and the at least one primary lateral sampling detector and a width of the interior of the chamber structure allows from one to at least 25 passes along a length of the chamber structure.

10. The sampling system of claim 1 wherein the at least one primary lateral sampling detector includes a photodiode response to at least some near-infrared wavelengths of the electromagnetic energy through at least some near-ultraviolet wavelengths of the electromagnetic energy.

11. The sampling system of claim 1 wherein the at least one primary lateral sampling detector includes at least one photodiode.

12. The sampling system of claim 11, further comprising:
at least one primary axial sampling detector positioned to detect electromagnetic energy from the interior of the chamber structure proximate the second end of the chamber structure, axially along the length of the chamber structure.

13. The sampling system of claim 12, further comprising a shroud having a proximal end and a distal end, the shroud extending at the proximate end thereof from the second end of the chamber structure, the shroud having an interior wall that is nonreflective, and wherein the at least one primary axial sampling detector is positioned at least proximate the distal end of the shroud.

14. The sampling system of claim 12 wherein the at least one primary axial sampling detector includes at least one a complementary metal oxide semiconductor (CMOS) detector, a charged coupled detector (CCD) detector, or a two-dimensional image detector.

15. The sampling system of claim 1, further comprising:
at least one port to selectively provide fluid communicative coupling between the interior and the exterior of the chamber structure.

16. The sampling system of claim 15 wherein the interior of the chamber structure is selectively sealable at pressures greater than one atmospheres.

17. The sampling system of claim 15 wherein the interior of the chamber structure is selectively sealable at pressures greater than X atmospheres.

18. A sampling system, comprising:
an elongated chamber structure to hold a fluid to be sampled, the elongated chamber structure having at least one wall that at least partially separates an interior of the chamber structure from an exterior thereof, the chamber structure having a first end and a second end, the second end opposite from the first end along a length of the chamber structure, at least a first portion of the elongated chamber structure reflective at least laterally across the interior of the chamber structure along at least a first portion of the length of the chamber structure;

a set of emitters positioned to emit electromagnetic energy into the interior of the chamber structure proximate the first end laterally across the interior of the chamber structure, and at an angle extending toward the second end from the first end;

at least one primary lateral sampling detector positioned to detect electromagnetic energy from the interior of the chamber structure proximate the second end of the chamber structure and laterally with respect to the length of the chamber structure;

at least one calibration detector positioned to detect electromagnetic energy from the interior of the chamber structure proximate the first end of the chamber structure and spaced relatively toward the second end with respect to the set of emitters; and at least one primary axial sampling detector positioned to detect electromagnetic energy from the interior of the chamber structure proximate the second end of the chamber structure, axially along the length of the chamber structure wherein the at least one primary lateral sampling detector includes at least one photodiode;

wherein at least a second portion of the elongated chamber structure is non-reflective at least laterally across the interior of the chamber structure along at least a second portion of the length of the chamber structure immediately preceding the at least one primary axial sampling detector.

* * * * *